US006866820B1

(12) United States Patent
Otto et al.

(10) Patent No.: US 6,866,820 B1
(45) Date of Patent: Mar. 15, 2005

(54) CLOSURE APPLIANCE FOR REAGENT CONTAINERS

(75) Inventors: Ralf Otto, Wiesbaden (DE); Hugo Wilmes, Bad Soden (DE); Hans-Dieter Sänger, Niedernhausen (DE)

(73) Assignee: Dade Behring Marburg, GmbH, Marburg (DE)

( * ) Notice: Subject to any disclaimer, the term of this patent is extended or adjusted under 35 U.S.C. 154(b) by 0 days.

(21) Appl. No.: 09/551,581

(22) Filed: Apr. 18, 2000

(30) Foreign Application Priority Data

Apr. 19, 1999 (DE) ......................................... 199 17 646

(51) Int. Cl.[7] .............................. B32B 5/02; B01L 3/02; B67B 7/18; B65D 39/00; B65D 43/26
(52) U.S. Cl. ........................... 422/63; 422/65; 422/100; 436/47; 436/180; 436/54; 81/3.42; 215/235; 215/236; 215/239; 215/240; 220/262; 220/281; 220/282; 222/562
(58) Field of Search ............................... 436/54, 43, 47, 436/49, 180; 220/262, 281, 282, 556, 810, 811, 812; 222/562; 215/235, 239, 240, 236; 422/63–65, 100, 104, 102; 81/3.2, 3.31, 3.33, 3.09

(56) References Cited

U.S. PATENT DOCUMENTS

| | | | | | |
|---|---|---|---|---|---|
| 4,455,280 A | * | 6/1984 | Shinohara et al. | .......... | 141/154 |
| 4,807,425 A | * | 2/1989 | Abrams | ..................... | 53/381.4 |
| 5,271,897 A | * | 12/1993 | Wurschum et al. | ......... | 422/100 |
| 5,289,930 A | * | 3/1994 | Inouye | ....................... | 206/223 |
| 5,481,946 A | * | 1/1996 | Nishikawa et al. | ........... | 81/3.2 |
| 5,578,494 A | | 11/1996 | Clark et al. | .................... | 436/54 |
| 5,628,962 A | * | 5/1997 | Kanbara et al. | ............ | 215/235 |
| 5,846,489 A | * | 12/1998 | Bienhaus et al. | ........... | 422/104 |
| 6,024,235 A | * | 2/2000 | Schwab | ...................... | 215/247 |
| 6,265,225 B1 | * | 7/2001 | Otto et al. | .................. | 215/236 |
| 6,531,096 B1 | | 3/2003 | Deveney et al. | .............. | 422/65 |
| 6,599,476 B1 | * | 7/2003 | Watson et al. | ................ | 422/63 |

FOREIGN PATENT DOCUMENTS

| | | |
|---|---|---|
| DE | 32 04 584 A1 | 9/1982 |
| DE | 33 46 517 A1 | 8/1984 |
| DE | 197 46 169 A 1 | 10/1997 |
| DE | 197 46 169 A1 | 4/1999 |
| EP | 0 509 281 B1 | 3/1992 |
| EP | 0 543 638 | 11/1992 |
| EP | 0 523 425 A1 | 1/1993 |
| EP | 0 703 457 A2 | 3/1996 |

OTHER PUBLICATIONS

Copy of European Search Report.

* cited by examiner

Primary Examiner—Jill Warden
Assistant Examiner—Brian R. Gordon
(74) Attorney, Agent, or Firm—Finnegan, Henderson, Farabow, Garrett and Dunner, L.L.P.

(57) ABSTRACT

The invention relates to an appliance for opening and closing a reagent-container stopper in a partially or fully automatic analysis apparatus, and to the method, which is applied by means of this appliance, for opening and closing a reagent-container stopper in a partially or fully automatic analysis appliance.

12 Claims, 16 Drawing Sheets

Section A-A

Section A-A

CLOSURE APPLIANCE FOR REAGENT CONTAINERS

BACKGROUND OF THE INVENTION

1. Field of the Invention

The invention relates to an appliance for opening and closing a reagent-container stopper in a partially or fully automatic analysis apparatus, and to the method, which is applied by means of this appliance, for opening and closing a reagent-container stopper in a partially or fully automatic analysis appliance.

2. Description of the Related Art

Partially or fully automatic analysis apparatus are in widespread use in medical diagnostics, but also in other fields, for example in analytics. These apparatus essentially comprise three components, a reagent part, a sample part and an analysis part. A certain number of reagents are stored in reagent containers in the reagent part. The reagents must as far as possible be hermetically sealed, in order to prevent contamination and evaporation. A certain number of samples are stored in the sample part. The samples too should also be as far as possible sealed in an airtight manner, possibly for safety reasons, e.g. contamination and potential risk of infection. Furthermore, it is advantageous for the individual compartments, i.e., for example, the entire reagent part or sample part, to be protected against contamination by means of a cover. The necessary transfer of liquids between the individual parts is generally carried out by means of transfer pipettes which, depending on the particular requirements, can move in the X-, Z- and/or Y-direction and/or in the phi-direction (angular rotation). This movement is often driven by stepper motors, in which case one motor is provided for each direction of movement. Owing to the different filling volumes and the different shapes of the reagent and/or sample containers—in the following text reagent and sample containers are referred to generally as reagent containers—the maximum movement in the Z-direction is under certain circumstances extremely great; it may be, for example, from 10 to 200 mm.

These requirements have led to various proposed solutions for the design of reagent-container stoppers. In this context, it is necessary to distinguish between two groups of solutions, on the one hand "passive" systems, in which the reagent-container stopper is designed in such a way that reclosure is to be ensured by the elasticity of the stopper material, as proposed, for example, in EP 0,509,281, and on the other hand "active" systems, in which opening and closing have to take place actively, as described, for example, in EP 0,543,638. However, this document does not provide any description of a possible solution to the question of how the above-described stopper can be opened or closed. The earlier application DE 197 46 169 describes an active reagent-container stopper which is moved by means of a plunger, but this document does not describe any possible way of executing this movement. In practice, the compartment cover presents additional problems. For the reasons listed above, the reagent containers should also only be open at the moment at which the removal is taking place.

SUMMARY OF THE INVENTION

The present invention is therefore based on the object of finding the most simple possible method for actuating an active reagent-container stopper. At the same time, the method is to be arranged in such a way that the appliances which are required for the method can, if appropriate, even be retrofitted to already existing apparatus.

This object is achieved by means of an appliance which essentially makes use of the existing vertical movement sequences of the pipette-needle carrier (4), without in doing so impairing the freedom of movement of the pipetting needle.

Advantageously, the upward movement of the pipette carrier is utilized, in that the upward movement of the pipette carrier is transmitted to the plunger (11) by means of a means which is known per se to the person skilled in the art and reverses the direction of movement, with the result that the plunger is moved downward out of the at-rest position into the working position. The utilization of the upward movement allows the plunger travel to be made independent of the immersion depth of the pipetting needle.

It is known to the person skilled in the art that, for example, forces can be transmitted in a wide variety of ways—e.g. by means of a suitable lever mechanism, a traction driver, a hydraulic appliance or a Bowden cable—so that the embodiments described below are simply intended to explain the invention, without limiting it in any way.

DETAILED DESCRIPTION OF THE PREFERRED EMBODIMENTS

One embodiment of the transfer appliance according to the invention is described by way of example in FIGS. 1 to 8:

1) the pipetting needle (3), which is suspended from a bearing arm (2), is moved into a position above the opening in the reagent container (12), which at this time is still closed;
2) the pipetting-needle carrier (4) is moved upward out of the displacement position, and in the process the movement is transmitted, via the catch (7), the rocker arm I (8), the stop rod (9) and the rocker arm II (10), to the plunger (11), which as a result is moved out of the at-rest position into the working position;
3) as a result of the horizontal movement of the reagent container on the guide (17) relative to the plunger, the lid of the reagent-container stopper is opened via the catch (15) and the reagent container is moved into the removal position;
4) as a result of the downward movement of the pipetting-needle carrier (4), in the reverse of the movement from step 2, plunger (11) is moved back into the at-rest position by means of spring force;
5) the pipetting needle (3) removes the transfer material;
6) the subsequent upward movement of the pipetting-needle carrier (4) results in the movement sequence from step 2 being repeated, with the result that plunger (11) is moved out of the at-rest position into the working position,
7) as a result of suitable movement of the reagent container relative to the plunger, the lid of the reagent-container stopper is closed by means of the catch (15), and the reagent container is moved into an at-rest position;
8) the transfer device is now ready for the next transfer operation.

Figure 1:
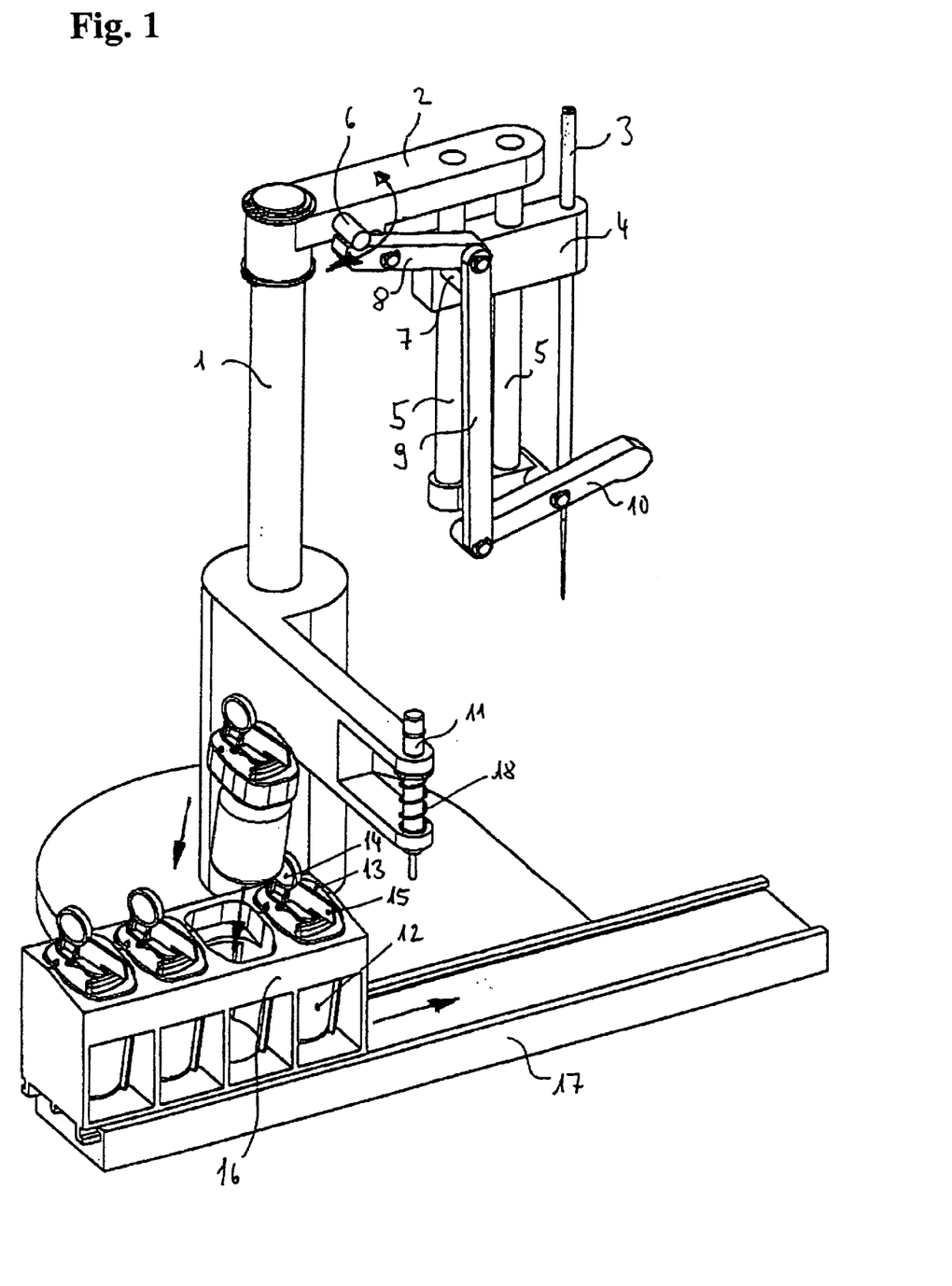
FIG. 1 shows the transfer appliance with the rocker arm mechanism in the displacement position.
Figure 2:
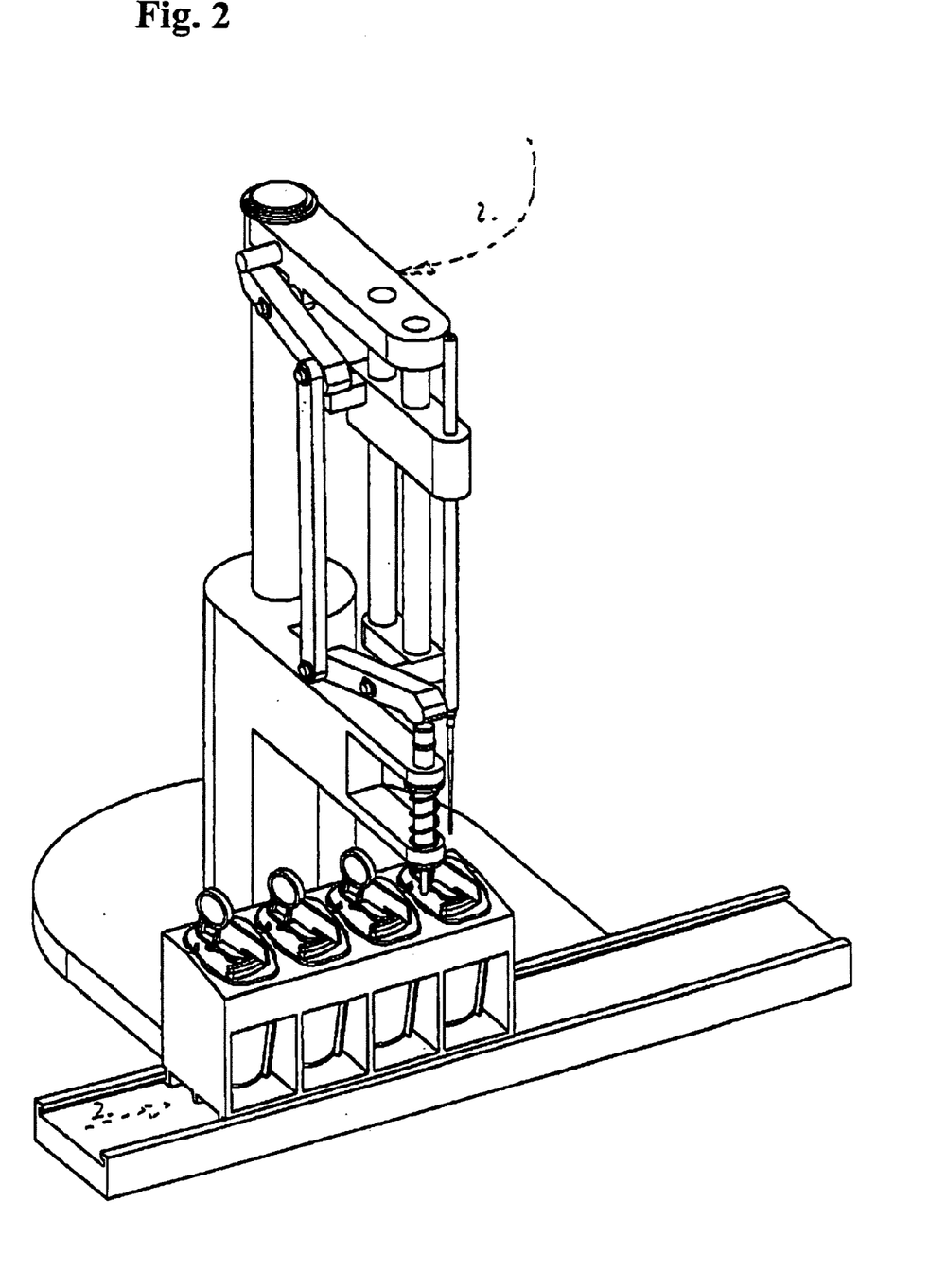
FIG. 2 is an isometric view of a first embodiment of the transfer appliance of FIG. 1 in the transfer position, the pipetting-needle carrier (4) in the displacement position, and the plunger (11) in the at-rest position.
Figure 3:
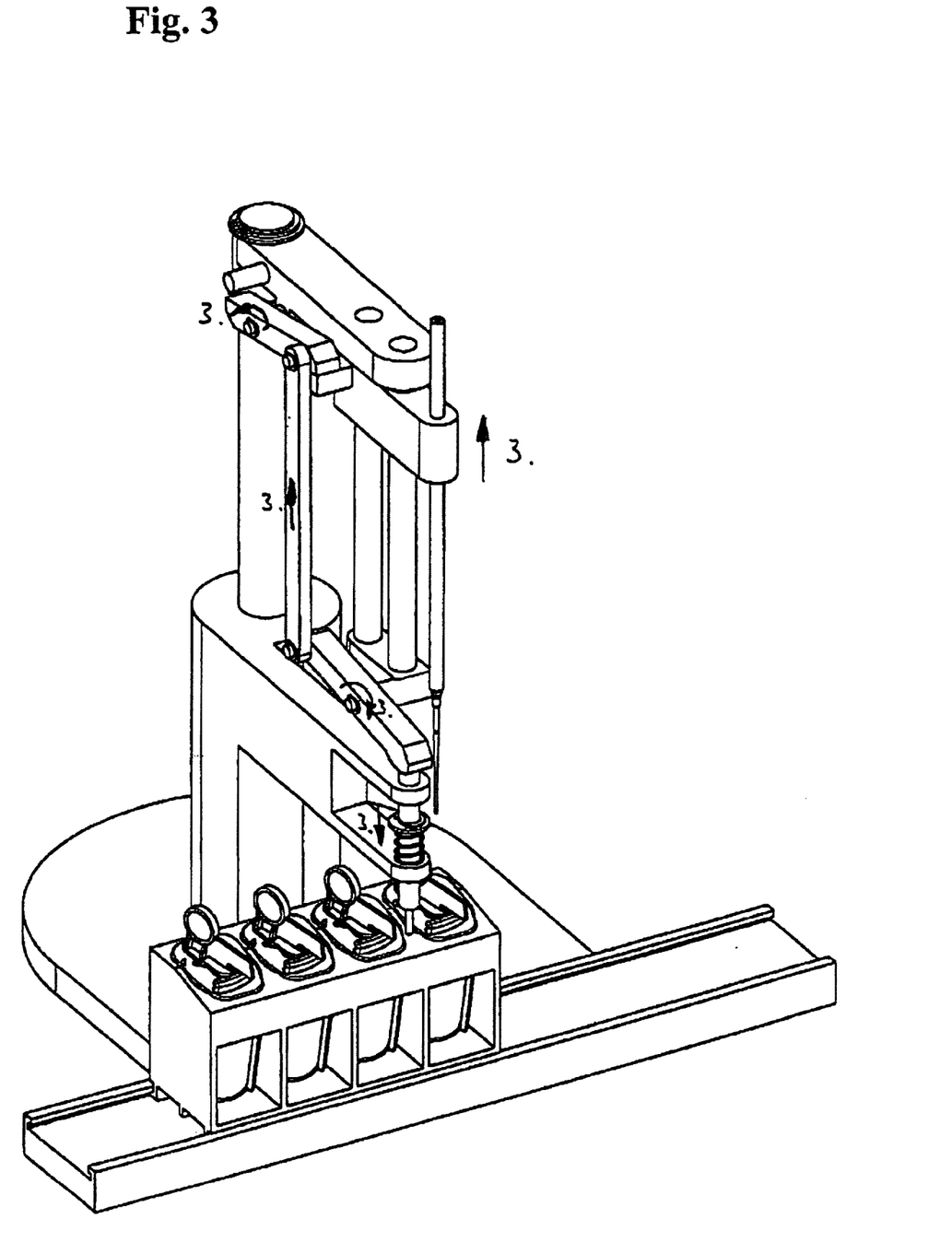
FIG. 3 is an isometric view of the transfer appliance of FIG. 1 with the pipetting-needle carrier (4) in the upper position, and the plunger (11) in the working position.
Figure 4:
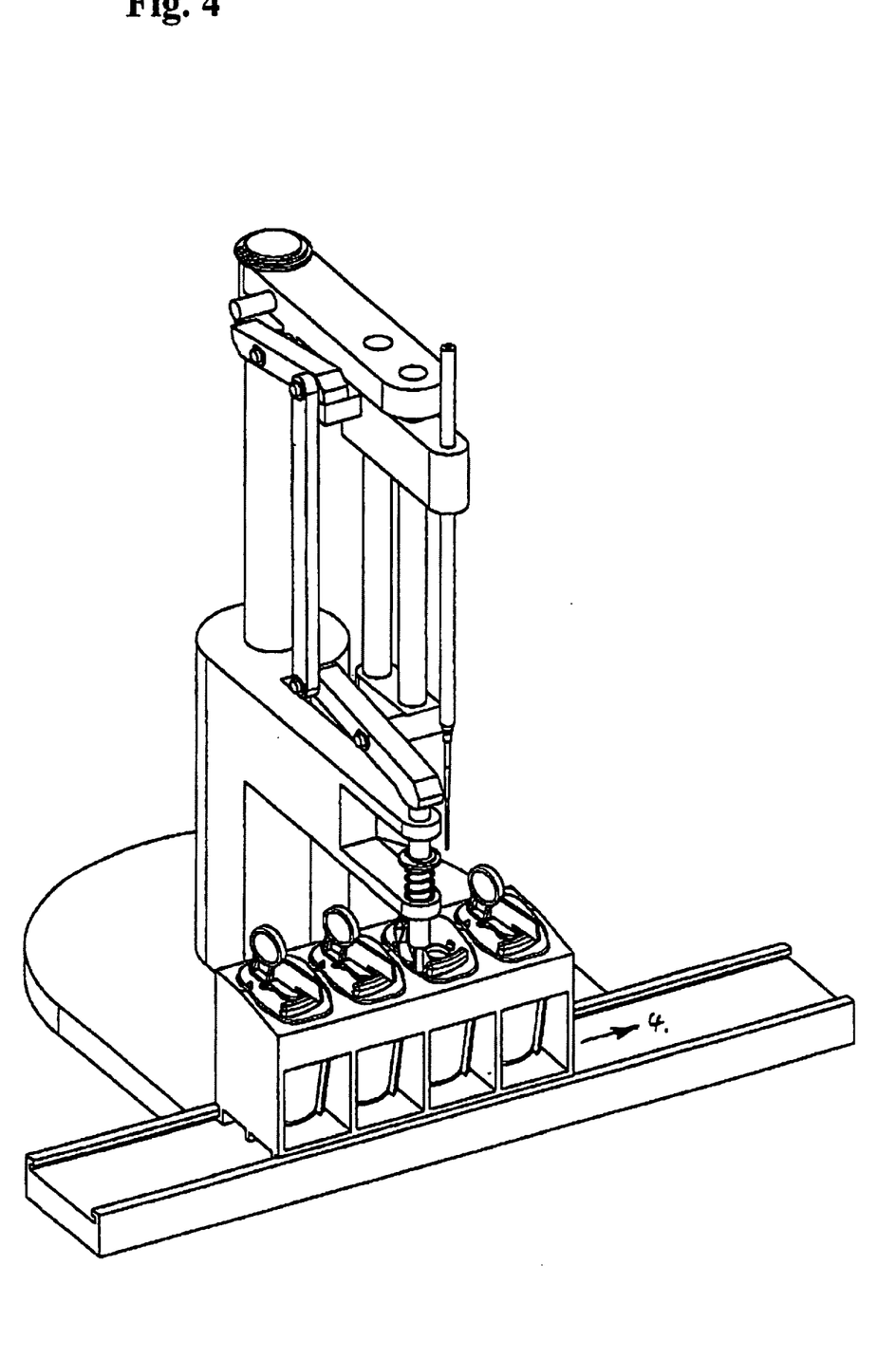
FIG. 4 is an isometric view of the transfer appliance of FIG. 1 with the plunger (11) in the working position, and the reagent-container carrier (16) in motion.
Figure 5:
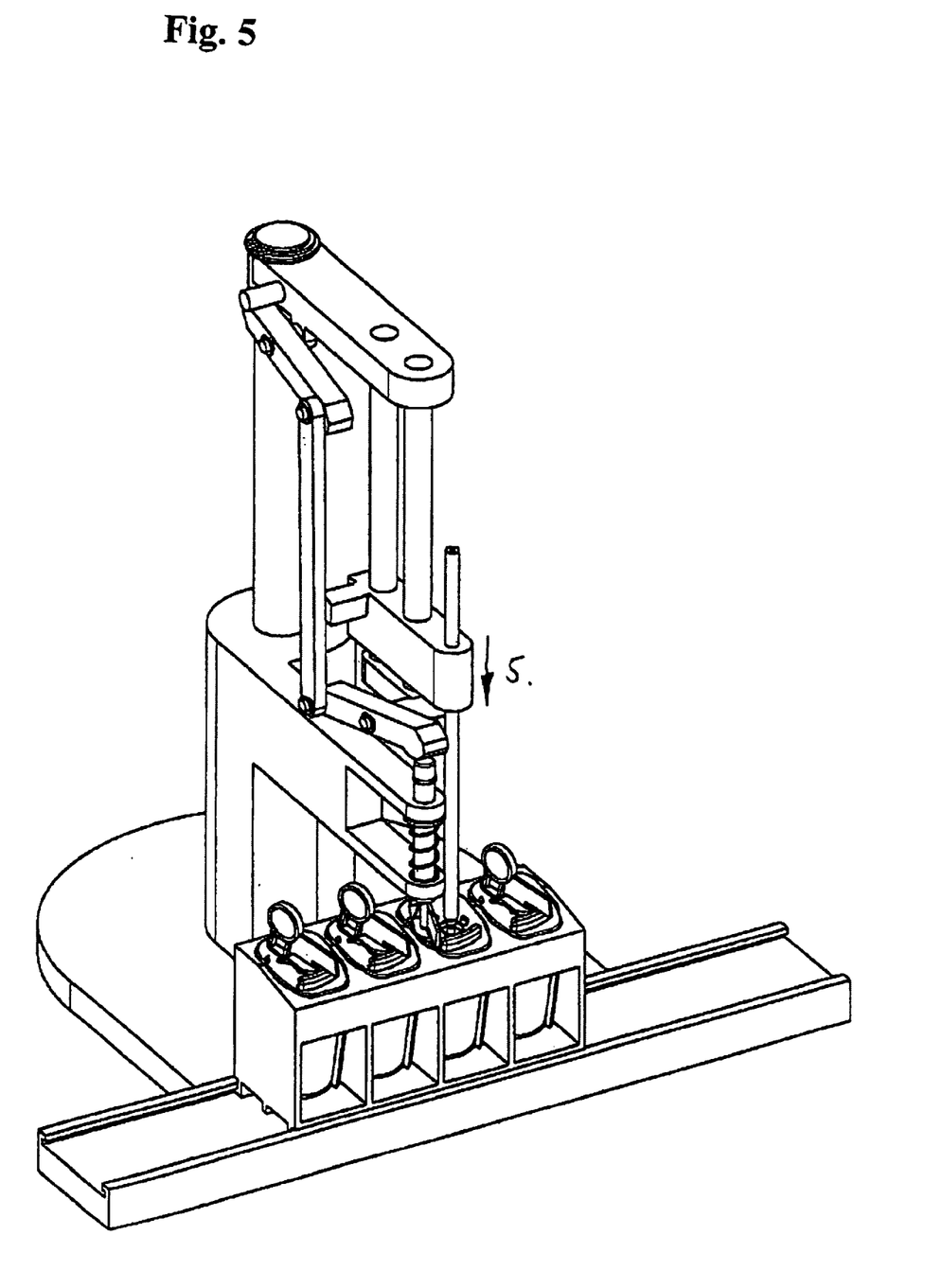
FIG. 5 is an isometric view of the transfer appliance of FIG. 1 with the reagent-container stopper (13) open, the pipetting needle in the pipetting position.
Figure 6:
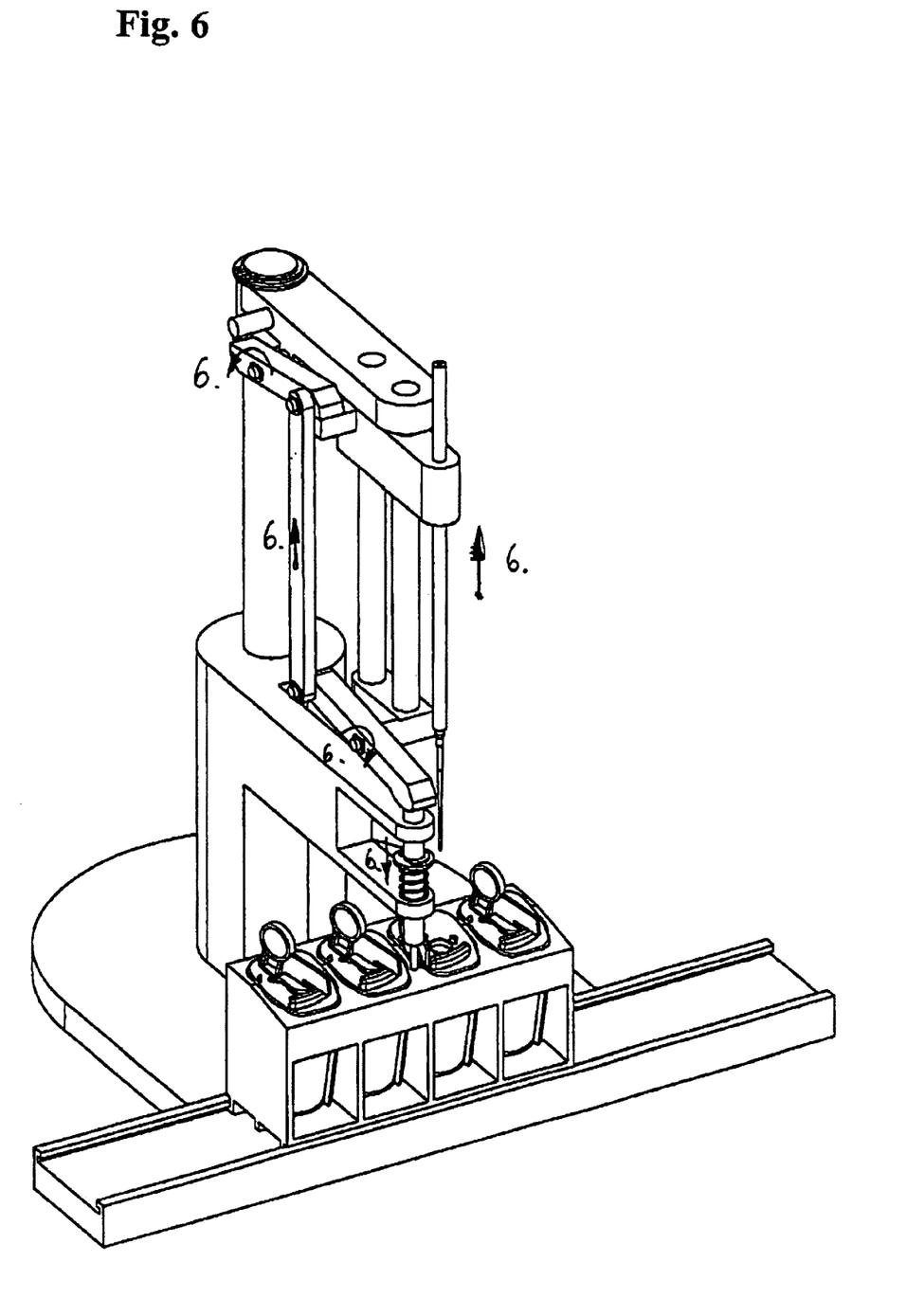
FIG. 6 is an isometric view of the transfer appliance of FIG. 1 with the pipetting-needle carrier (4) in the upper position, and the plunger (11) in the working position.
Figure 7:
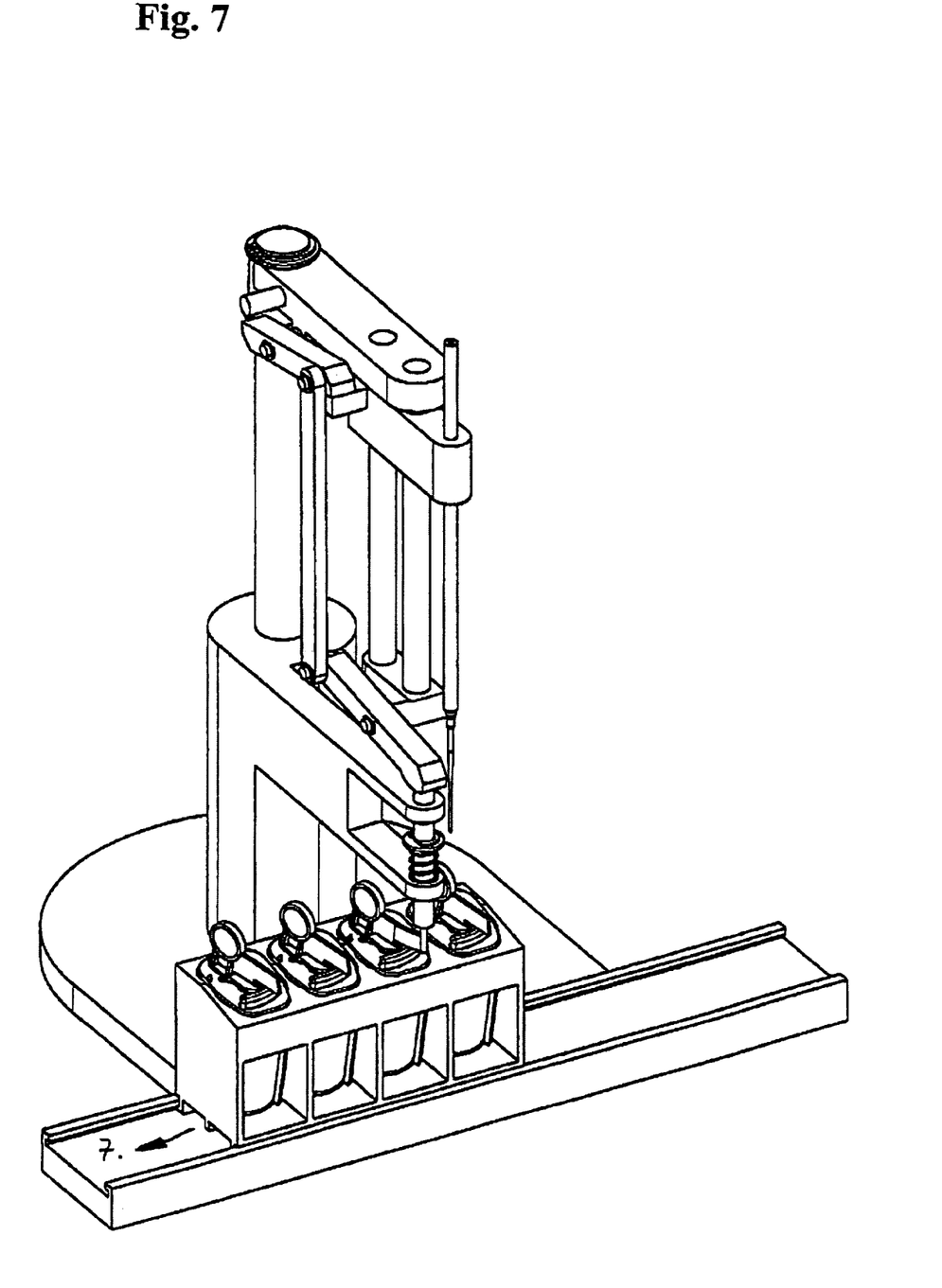
FIG. 7 is an isometric view of the transfer appliance of FIG. 1 with the pipetting-needle carrier (4) in the upper position, the plunger (11) in the working position, the reagent-container stopper (13) closed, and the catch (15) elastically deflected.
Figure 8:
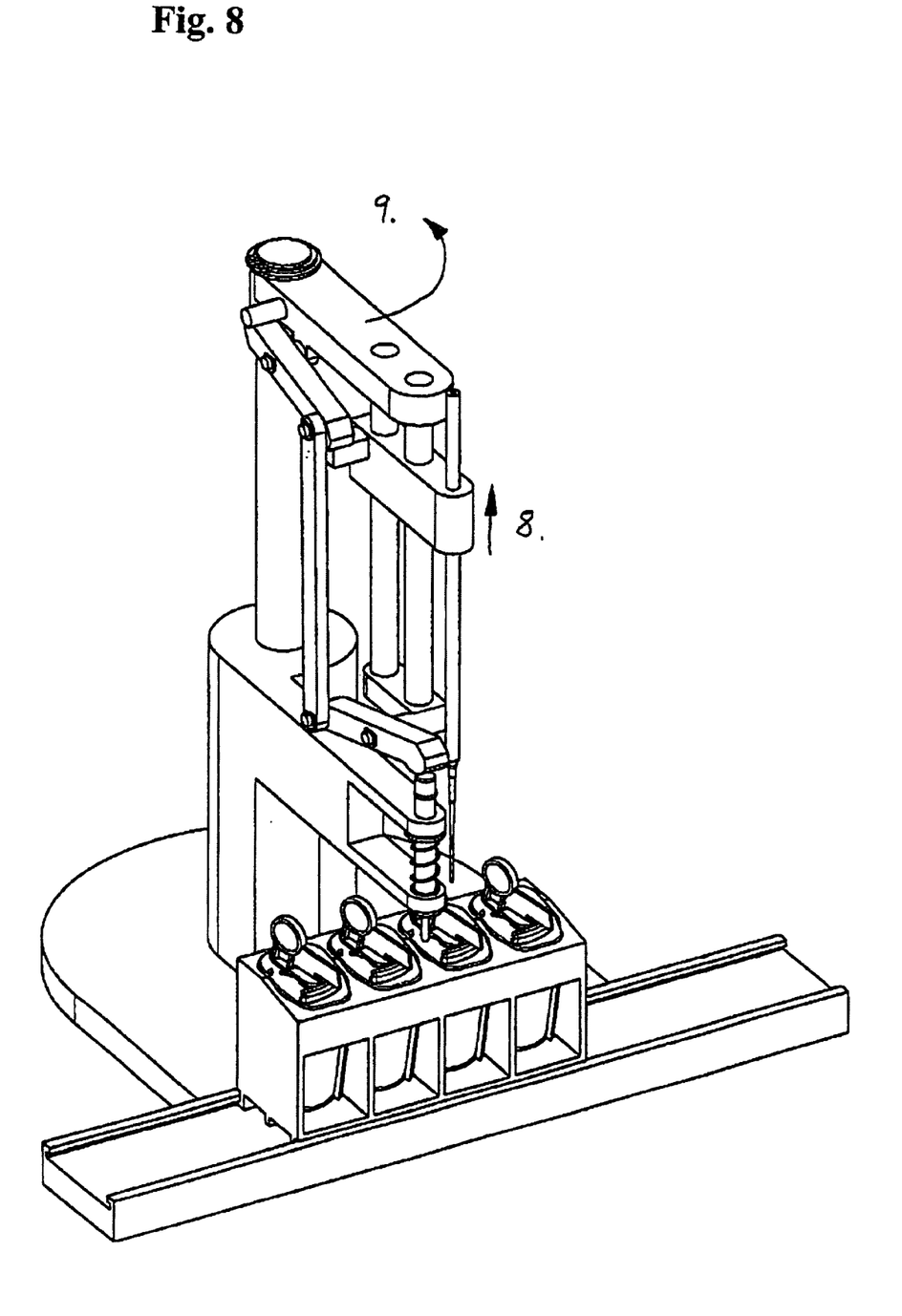
FIG. 8 is an isometric view of the transfer appliance of FIG. 1 pivoting into the displacement position, the pipetting-needle carrier (4) in the displacement position, the plunger (11) in the at-rest position.
Figure 9:
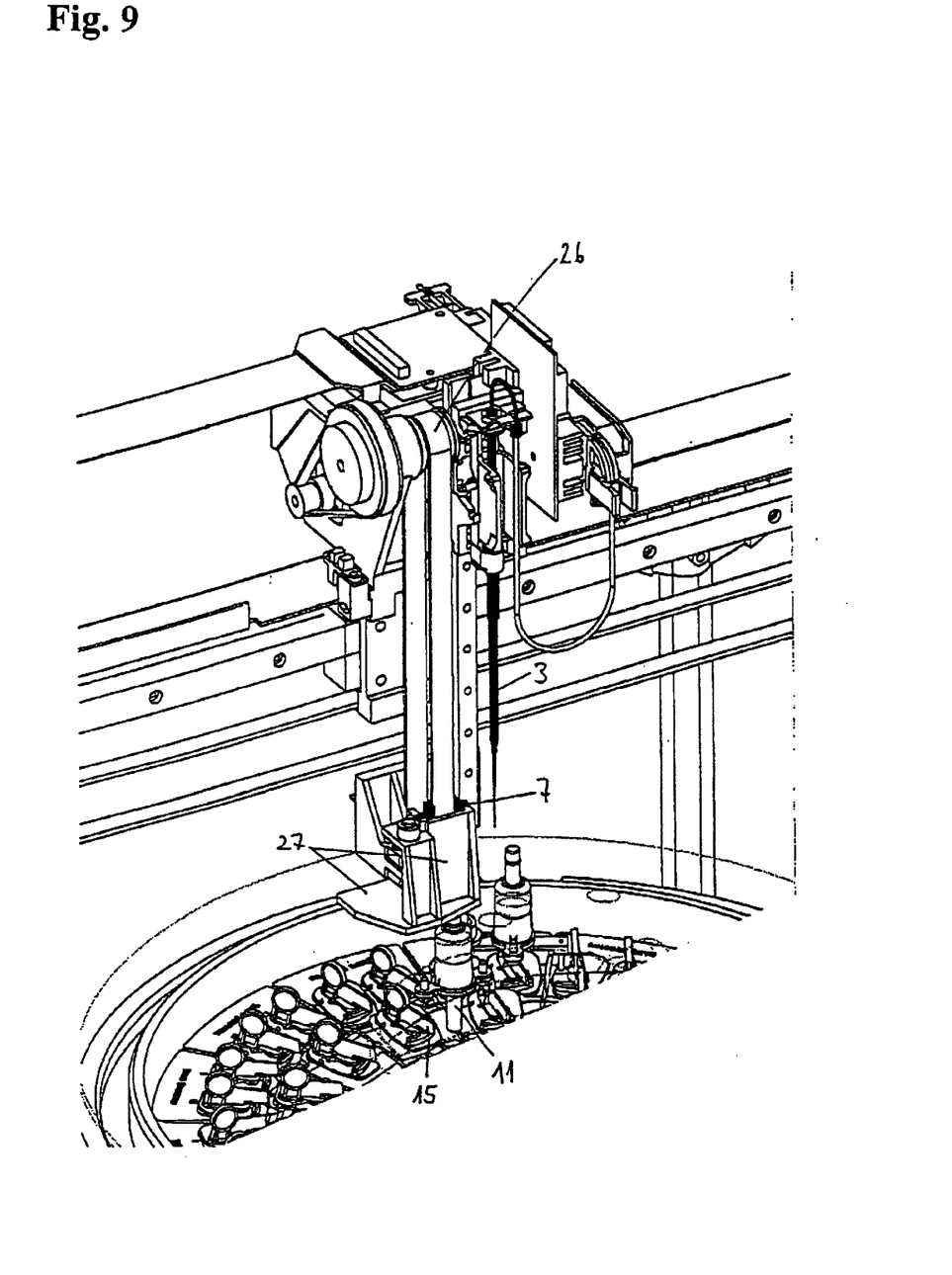
FIG. 9 is a partial isometric view of a second embodiment of a transfer appliance according to the present invention, the transfer appliance with the toothed belt (26) in the transfer position, the pipetting-needle carrier (4) in the upper position, and the ram (11) in the working position.
Figure 10:
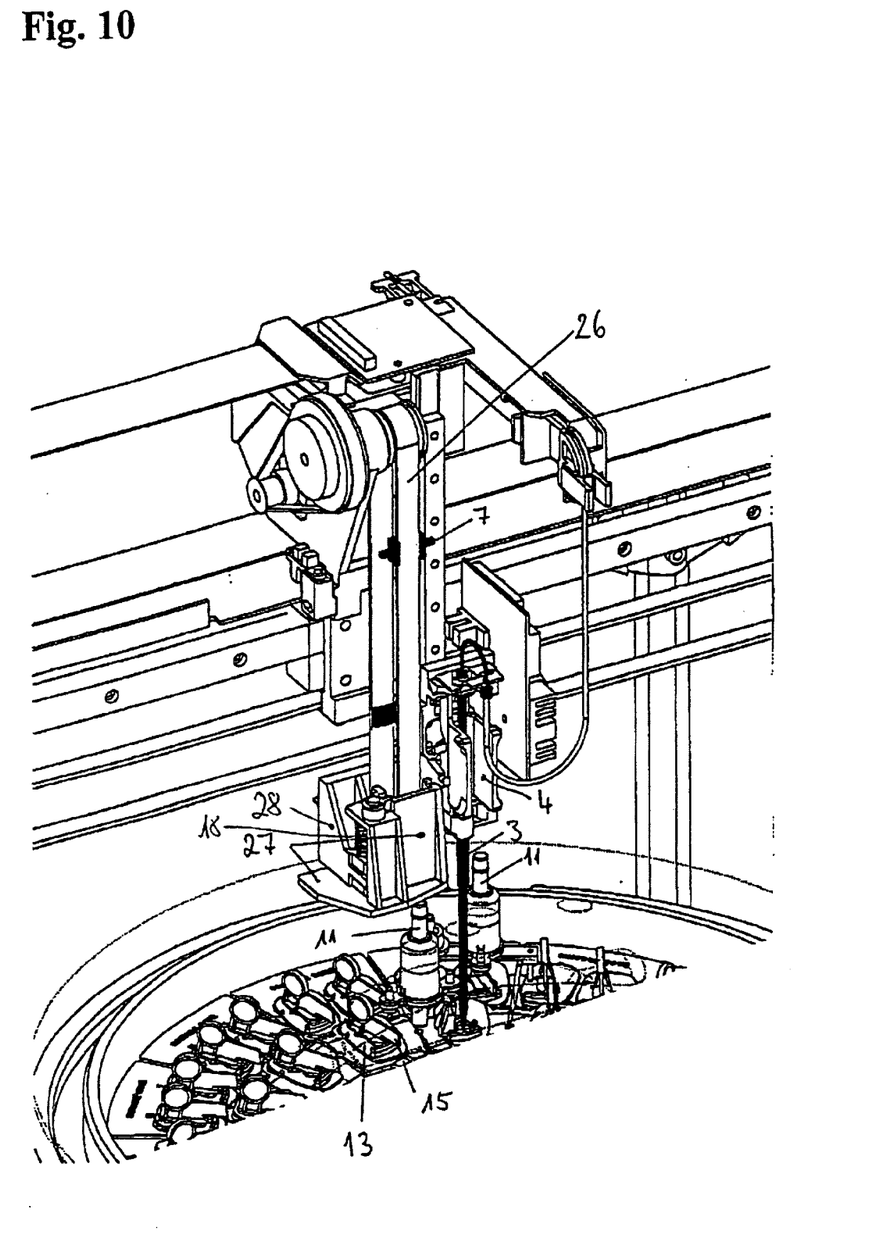
FIG. 10 is a partial isometric view of the device of FIG. 9 with the transfer appliance in the displacement position, the pipetting-needle carrier in the displacement position, and the thrust plate (27) in the at-rest position.

FIGS. 9 and 10 show an alternative advantageous configuration of the transfer appliance according to the invention. In a similar manner to the exemplary embodiment described above, in this embodiment the movement of the toothed belt (26), which moves the pipetting-needle carrier (4), is utilized in order to move the plunger (11).

Further embodiments are described in the patent claims.

The pipetting-needle carrier (4) is moved upward out of the displacement position, and in the process the movement is transmitted, via the catch (7) and a thrust plate (27), to the plunger (11), which consequently is moved out of the at-rest position into the working position.

The use of a thrust plate allows even a plunger which is at a three-dimensional distance from the removal position to be moved, so that consequently there is a greater degree of freedom in the design of the actual embodiment of the invention.

The reagent-container stoppers may be designed in many ways. For example, EP 0,543,638 describes reagent-container stoppers which are opened by a rocker mechanism which can be moved by the plunger (10) according to the invention. DE 197 46 169 describes reagent-container stoppers which are essentially distinguished by the fact that the lids can be pivoted upward and sideways by means of an inclined, bistable hinge.

Figure 11:
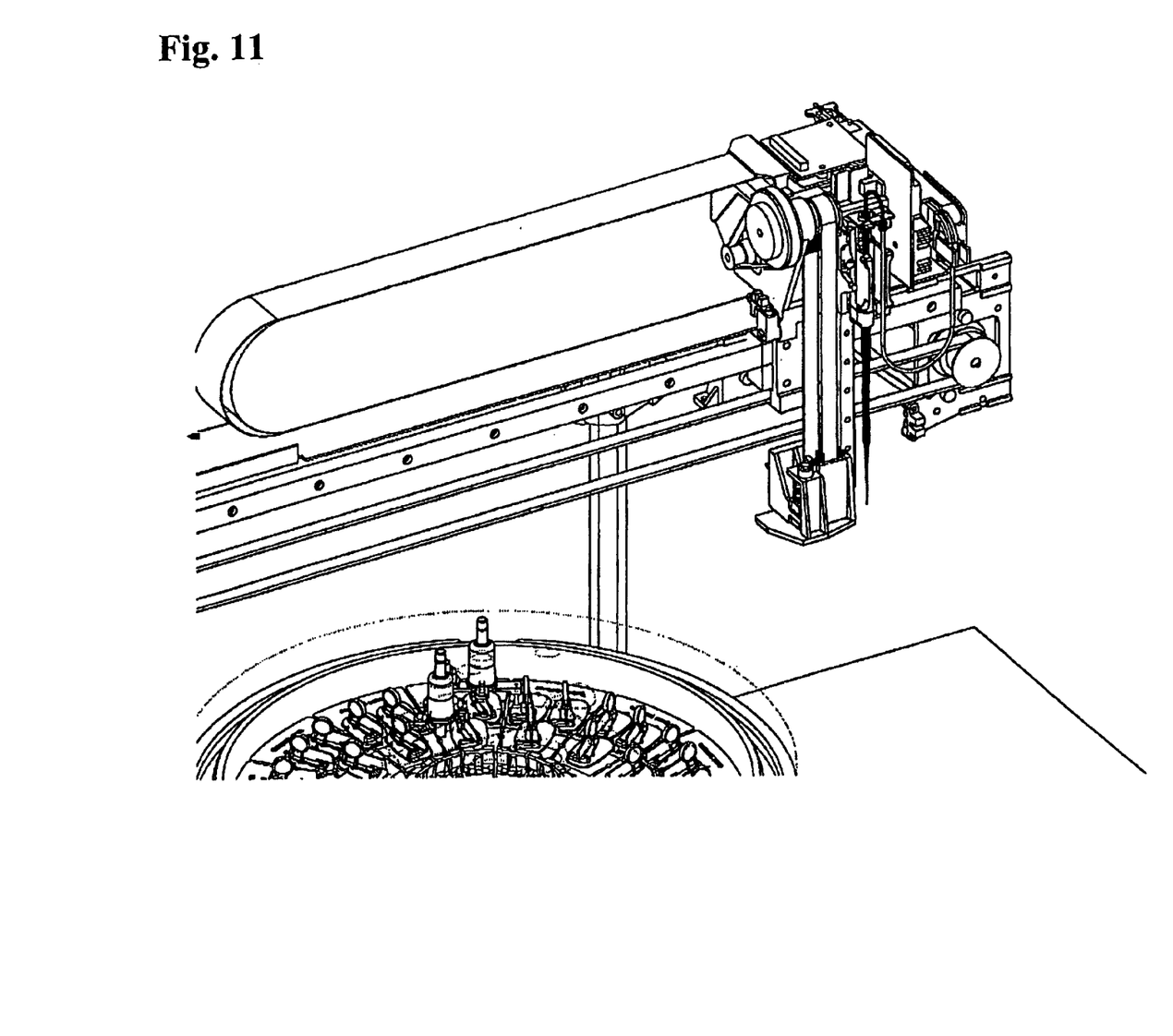
FIG. 11 shows the reagent-container stopper (13) open, the pipetting needle in the pipetting position, the plunger (11) in the at-rest position.

It is advantageously also possible to use, for example, the two-piece reagent-container stoppers illustrated in FIGS. 9 to 11. The reagent-container stopper (13) comprises a reagent-container stopper lid (14) and the reagent-container stopper body (19). The two parts are connected to one another by means of a coupling pin (20). The material used is advantageously a partially elastic plastics material, such as for example polypropylene for the reagent-container stopper lid (14) and polyethylene for the reagent-container stopper body (19). The substantially horizontal movement of the lid in a single plane allows this reagent-container stopper to be of very simple structure. The opening (21) is advantageously sealed by the lid (22) by designing the seal (21/22) in the shape of a segment of a sphere.

A particularly well-sealed closure of the lid can be achieved if a lug (23) is arranged on the lid, which lug runs in a guide (24) and thus ensures a pressure-loaded seal between the lid and the opening (21).

The advantageous design of the seal in the shape of a segment of a sphere makes it possible to dispense with a special sealing insert.

The reliability of the analysis results can be visually improved still further by means of the reagent-container stopper according to the invention by providing the reagents which are required for a specific detection with reagent-container stoppers which are of the same color.

Figure 12:
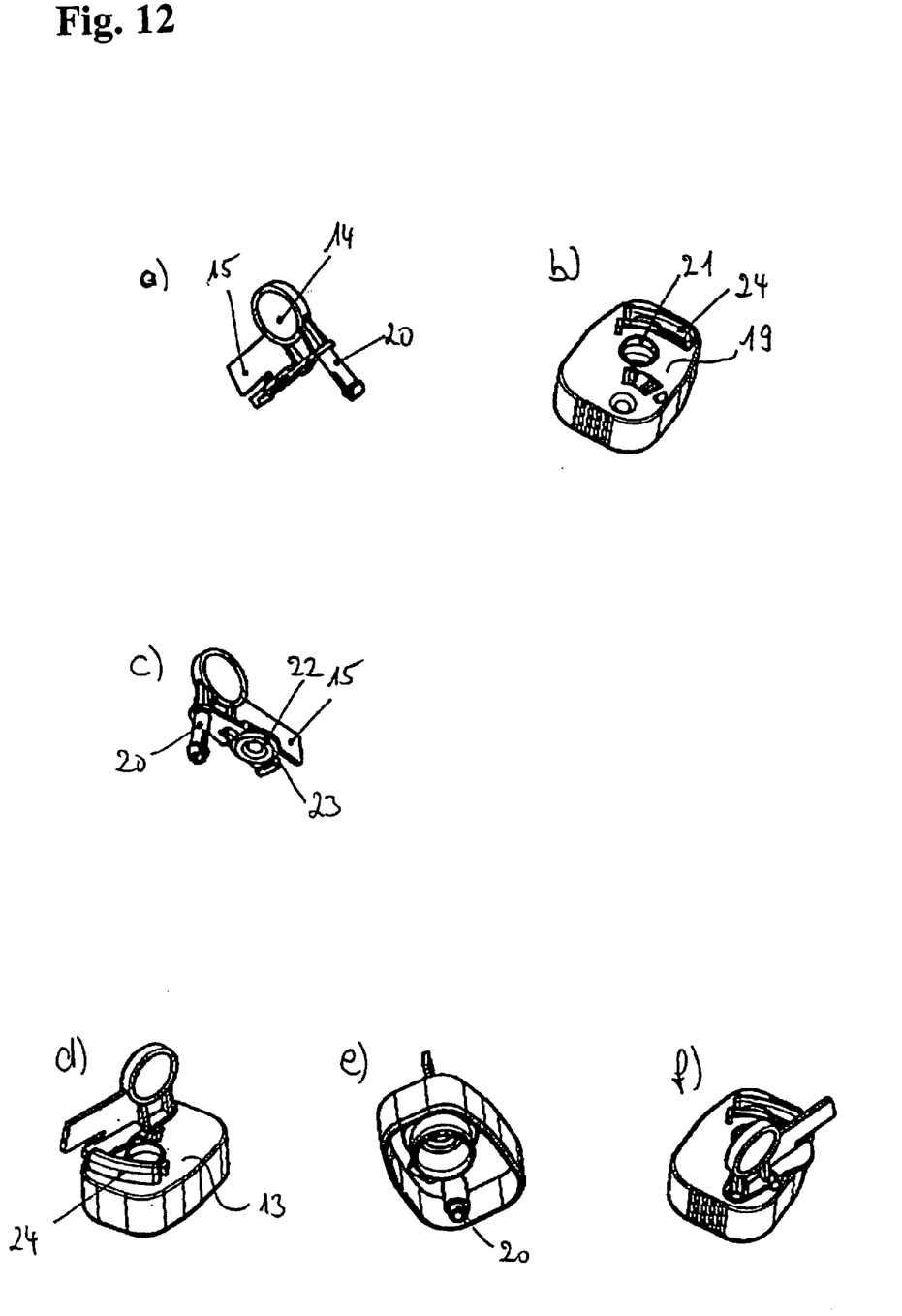
FIGS. 12a–12f are various isometric views of the reagent-container stopper (13), dismantled into reagent-container stopper lid (14) and reagent-container stopper body (19)
Figure 13:
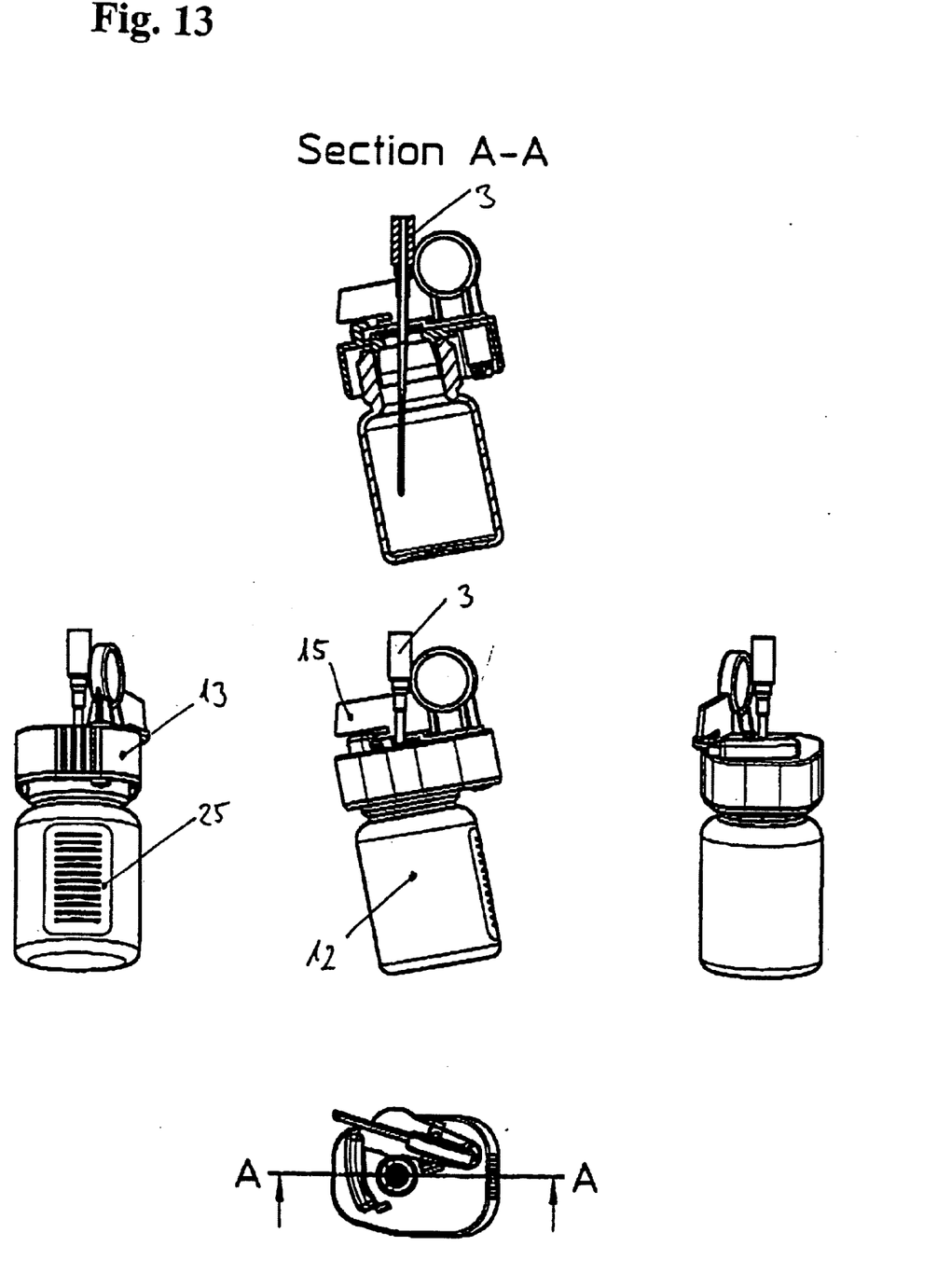
FIG. 13a is a top view of an open stopper lid of a reagent container according to the present invention.
FIG. 13b is a cross-sectional view of the reagent container of FIG. 13a taken along line A—A.
FIGS. 13c–13e are various isometric views of the reagent container (12) with reagent-container stopper (13) open.
Figure 13A:
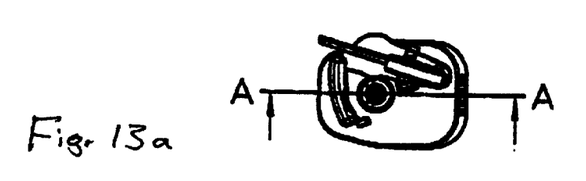
Figure 13B:
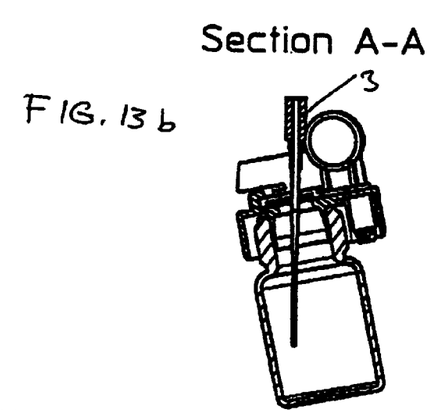
Figure 13C:
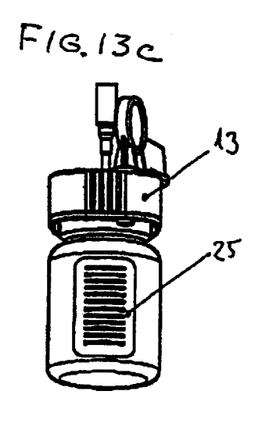
Figure 13D:
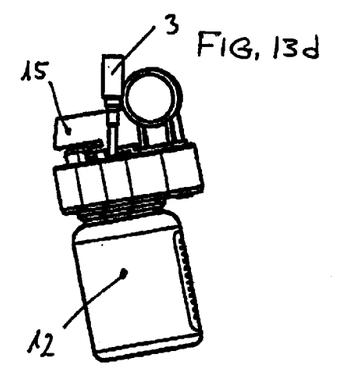
Figure 13E:
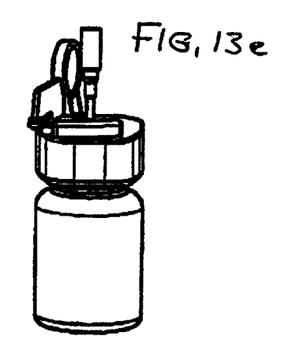
Figure 14:
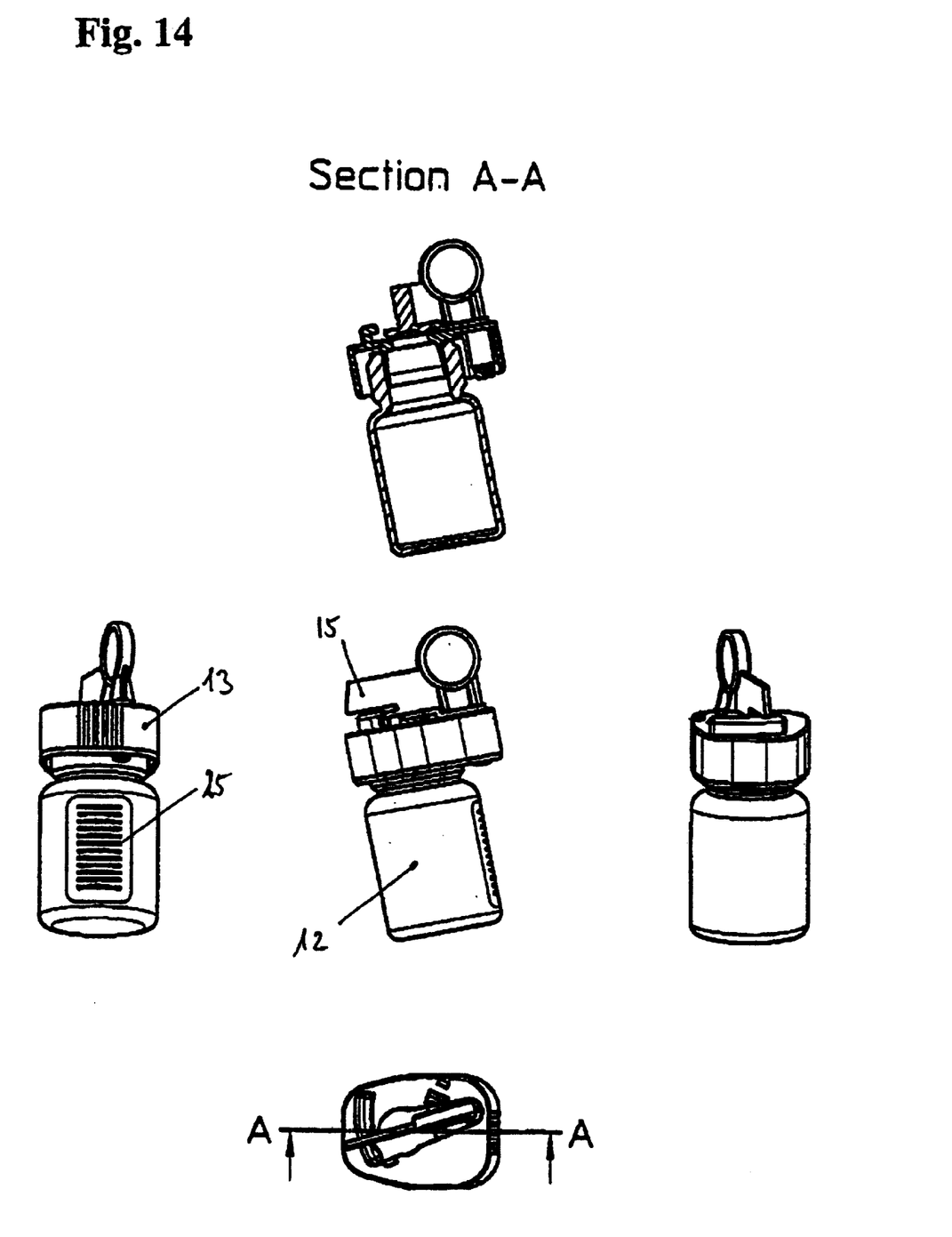
FIG. 14a is a top view of a closed stopper lid of a reagent container according to the present invention.
FIG. 14b is a cross-sectional view of the reagent container of FIG. 14a taken along line A—A.
FIGS. 14c–14e are various isometric views of the reagent container (12) with reagent-container stopper (13) closed.
Figure 14A:
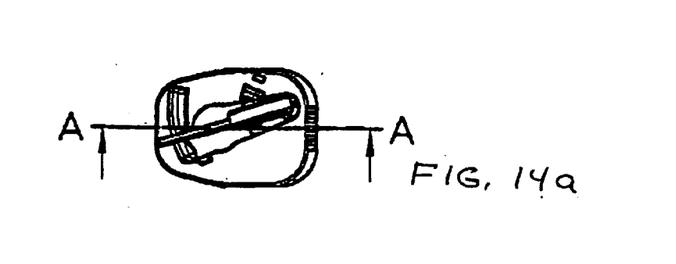
Figure 14C:
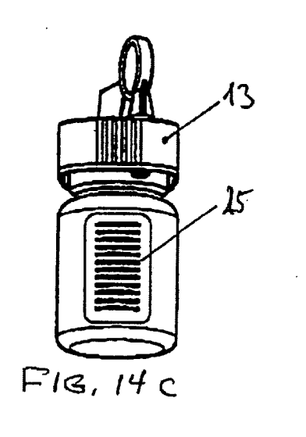
Figures 14D, 14E:
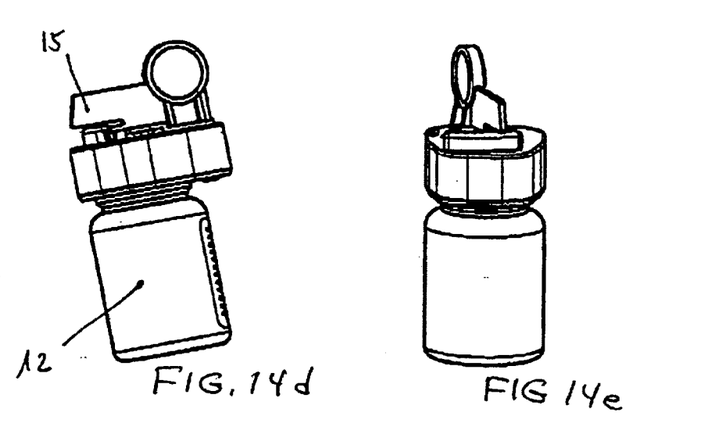

FIGS. 12 and 13 show the reagent container with the reagent-container stopper according to the invention in the open and closed positions, respectively. While the reagent-container stopper may be made from one or more different plastics materials, the reagent container itself is preferably made from a transparent plastics material or glass. It is particularly advantageous for it to be possible for reagent vessels of different designs to be closed using the same reagent-container stopper according to the invention and to be inserted into an automatic analyzer in this way.

The reagent-container stopper is opened and closed by the plunger (11), which moves relative to the reagent container, engages on a catch (15) arranged on the stopper which is to be opened and opens the lid at a predetermined position. The plunger (11), which causes the reagent-container stopper to open and close, can be actuated by the appliance according to the invention. The catch (15) is preferably designed in such a way that, in the limit position, it can be elastically deflected so far by the plunger that the plunger (11) can be moved beyond the limit position on the reagent container.

LIST OF REFERENCE NUMERALS (1) rotatable support column
(2) bearing arm
(3) pipetting needle
(4) pipetting-needle carrier, vertically movable
(5) vertical guide for the pipetting-needle carrier (4)
(6) abutment
(7) catch
(8) rocker arm I
(9) stop rod
(10) rocker arm II
(11) plunger (12) reagent container
(13) reagent-container stopper
(14) reagent-container stopper lid
(15) partially elastic catch
(16) reagent-container carrier, horizontally movable
(17) guide for the reagent-container carrier
(18) restoring spring
(19) reagent-container stopper body
(20) coupling pin
(21) bottom shell of the seal, in the shape of a segment of a sphere
(22) top shell of the seal, in the shape of a segment of a sphere
(23) guide lug
(24) guide
(25) bar code
(26) toothed belt
(27) thrust plate
(28) thrust-plate abutment

What is claimed is:

1. An appliance for opening and closing reagent container stoppers in a partially or fully automated analysis apparatus, wherein said apparatus includes a pipetting-needle carrier and said appliance comprises: a plunger for opening and closing a reagent container stopper by engaging and releasing a catch on the reagent container stopper, the plunger movable between an at rest position and a working position; an automatic conveyor for moving the reagent container relative to the plunger, wherein the conveyor is movable in a first direction to place the plunger in a position to open the stopper, and wherein the conveyor is movable in a second direction, opposite to the first direction, to place the plunger in a position to close the stopper; and a structure for translating movement of a pipetting-needle carrier to the plunger to cause movement of the plunger wherein the structure for translating movement includes means for moving the plunger in a downward direction in response to movement of the pipetting-needle carrier in an upward direction.

2. The appliance of claim 1, wherein the structure for translating movement includes two rocker arms and a stop rod, the stop rod being connected to and positioned between the two rocker arms, the stop rod also being connected to the pipetting-needle carrier, such that the stop rod moves with the pipetting-needle carrier.

3. The appliance of claim 1, further comprising a traction drive for moving the pipetting-needle carrier.

4. The appliance of claim 2, wherein one of the rocker arms is rotatably connected to a first end of the stop rod and wherein the other of the rocker arms is rotatably connected to an opposite end of the stop rod.

5. The appliance of claim 4, wherein vertical movement of the pipetting-needle carrier results in rotational movement of the rocker arms with respect to the stop rod.

6. The appliance of claim 1, wherein the structure for translating movement includes a thrust plate and a catch member, wherein the thrust plate is engagable with the plunger, and wherein the catch member is connected to a means for driving the pipetting-needle carrier, such that the movement of the pipetting-needle carrier in a first direction results in movement of the catch member and thrust plate in a second direction opposite the first direction.

7. An appliance for opening and closing reagent container stoppers in partially or fully automatic analysis apparatus, comprising:

a plunger for opening and closing a reagent container stopper by engaging and releasing a catch on the reagent container stopper, the plunger movable between an at rest position and a working position;

an automatic conveyor for moving the reagent container relative to the plunger, wherein the conveyor is movable in a first direction to place the plunger in a position to open the stopper, and wherein the conveyor is movable in a second direction, opposite to the first direction, to place the plunger in a position to close the stopper; and a structure for translating movement of a pipetting-needle carrier to the plunger to cause movement of the plunger, wherein the structure for translating movement includes a thrust plate and a catch member, wherein the thrust plate is engagable with the plunger, and wherein the catch member is connected to a means for driving the pipetting-needle carrier, such that movement of the pipetting-needle carrier in a first direction results in movement of the catch member and thrust plate in a second direction opposite the first direction.

8. The appliance of claim 7, wherein the structure for translating movement includes means for moving the plunger in a downward direction in response to movement of the pipetting-needle carrier in an upward direction.

9. The appliance of claim 8, wherein the structure for translating movement includes two rocker arms and a stop rod, the stop rod being connected to and positioned between the two rocker arms, the stop rod also being connected to the pipetting-needle carrier, such that the stop rod moves with the pipetting-needle carrier.

10. The appliance of claim 7, further comprising a traction drive for moving the pipetting-needle carrier.

11. The appliance of claim 9, wherein one of the rocker arms is rotatably connected to a first end of the stop rod and wherein the other of the rocker arms is rotatably connected to an opposite end of the stop rod.

12. The appliance of claim 11, wherein vertical movement of the pipetting-needle carrier results in rotational movement of the rocker arms with respect to the stop rod.

* * * * *